(12) United States Patent
Phillips et al.

(10) Patent No.: US 12,213,703 B2
(45) Date of Patent: Feb. 4, 2025

(54) THREE DIMENSIONAL DISTRACTORS

(71) Applicant: DEPUY SYNTHES PRODUCTS, INC., Raynham, MA (US)

(72) Inventors: Emma Phillips, West Chester, PA (US); John Noon, Swarthmore, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 479 days.

(21) Appl. No.: 17/678,727

(22) Filed: Feb. 23, 2022

(65) Prior Publication Data
US 2023/0263556 A1    Aug. 24, 2023

(51) Int. Cl.
| | | |
|---|---|---|
| *A61B 17/64* | (2006.01) | |
| *A61B 17/66* | (2006.01) | |
| *A61B 17/68* | (2006.01) | |
| *A61B 17/80* | (2006.01) | |
| *A61B 90/00* | (2016.01) | |
| *B33Y 80/00* | (2015.01) | |
| *A61B 17/00* | (2006.01) | |

(52) U.S. Cl.
CPC .............. *A61B 17/64* (2013.01); *A61B 17/66* (2013.01); *A61B 17/8019* (2013.01); *A61B 90/03* (2016.02); *B33Y 80/00* (2014.12); *A61B 2017/00526* (2013.01); *A61B 2017/681* (2013.01); *A61B 2090/035* (2016.02)

(58) Field of Classification Search
CPC ......... A61B 17/60; A61B 17/64; A61B 17/66; A61B 17/663; A61B 2017/681; A61B 17/8004
See application file for complete search history.

(56) References Cited

U.S. PATENT DOCUMENTS

| | | |
|---|---|---|
| 5,769,850 A | 6/1998 | Chin |
| 5,807,382 A | 9/1998 | Chin |
| 5,810,812 A | 9/1998 | Chin |

(Continued)

FOREIGN PATENT DOCUMENTS

| | | |
|---|---|---|
| CN | 110693588 A | 1/2020 |
| CN | 212913344 U | 4/2021 |
| WO | 2011/038209 A2 | 3/2011 |

OTHER PUBLICATIONS

International Search Report & Written Opinion for PCT/IB2023/051079 mailed on Jul. 21, 2023.

*Primary Examiner* — Larry E Waggle, Jr.
(74) *Attorney, Agent, or Firm* — Kramer & Amado, P.C.

(57) ABSTRACT

A helical distractor, including: a distractor body having an open tubular shape including: a fixed footplate attached to a first end of the distractor body; first and second body edges; first and second key grooves in the first and second body edges, respectively; and an end cap at a second end of the distractor body; a movable foot including: body threads; a first key configured to engage the first key groove; a second key configured to engage the second key groove; and a movable footplate; an advancement screw with a threaded portion inside the distraction body, wherein the threaded portion is configured to engage the body threads of the movable foot, wherein the movable foot moves along the distractor body when the advancement screw is rotated, and wherein the distractor body is configured to cause the movable foot to rotate as it moves along the distractor body.

21 Claims, 12 Drawing Sheets

(56) References Cited

U.S. PATENT DOCUMENTS

| | | |
|---|---|---|
| 5,899,940 A | 5/1999 | Carchidi et al. |
| 5,976,142 A | 11/1999 | Chin |
| 6,019,769 A | 2/2000 | McCarthy et al. |
| 6,062,854 A | 5/2000 | Pozzi |
| 6,113,599 A | 9/2000 | Landsberger |
| 6,139,316 A * | 10/2000 | Sachdeva ............... A61C 7/10 433/7 |
| 6,302,687 B1 | 10/2001 | King |
| 6,322,566 B1 | 11/2001 | Triaca et al. |
| 6,358,255 B1 | 3/2002 | Testa |
| 6,423,069 B1 | 7/2002 | Sellers |
| 6,589,250 B2 | 7/2003 | Schendel |
| 6,884,243 B2 | 4/2005 | Sellers |
| 6,887,275 B2 | 5/2005 | Carchidi et al. |
| 6,908,469 B2 | 6/2005 | Sellers et al. |
| 7,182,785 B2 | 2/2007 | Elsalanty et al. |
| 7,252,668 B2 | 8/2007 | Wolgen |
| 7,322,987 B2 | 1/2008 | Schendel |
| 7,485,121 B2 | 2/2009 | Noon et al. |
| 7,588,579 B2 | 9/2009 | Mommaerts |
| 7,621,922 B2 | 11/2009 | Schendel et al. |
| 7,686,836 B2 | 3/2010 | Johnston et al. |
| 7,862,566 B2 | 1/2011 | Posnick |
| 7,875,033 B2 | 1/2011 | Richter et al. |
| 7,892,241 B2 | 1/2011 | Posnick |
| 7,981,118 B2 | 7/2011 | Mommaerts |
| 7,998,216 B2 | 8/2011 | Elsalanty et al. |
| 8,172,849 B2 | 5/2012 | Noon et al. |
| 8,282,635 B1 | 10/2012 | Amato |
| 8,287,573 B2 | 10/2012 | Mulone |
| 8,491,582 B2 * | 7/2013 | Keilen ................... A61B 17/66 606/57 |
| 8,529,579 B2 | 9/2013 | Bulloch et al. |
| 8,808,290 B2 | 8/2014 | Dubois |
| 8,858,566 B2 | 10/2014 | Noon et al. |
| 8,979,858 B2 | 3/2015 | Gordon et al. |
| 9,055,976 B2 | 6/2015 | Li |
| 9,113,958 B2 | 8/2015 | Coceancig |
| 9,271,780 B2 | 3/2016 | Noon et al. |
| 9,308,026 B2 | 4/2016 | Ruiz |
| 9,622,782 B1 | 4/2017 | Alruhaimi |
| 9,622,801 B1 | 4/2017 | Alruhaimi |
| 9,700,353 B2 | 7/2017 | Harris et al. |
| 10,166,053 B2 | 1/2019 | Kubis et al. |
| 10,433,887 B2 | 10/2019 | Noon et al. |
| 10,467,356 B2 | 11/2019 | Davison et al. |
| 10,492,840 B2 | 12/2019 | Ruiz |
| 10,695,112 B2 * | 6/2020 | Noon ..................... A61B 17/66 |
| 2021/0244444 A1 | 8/2021 | Lazarovici |

* cited by examiner

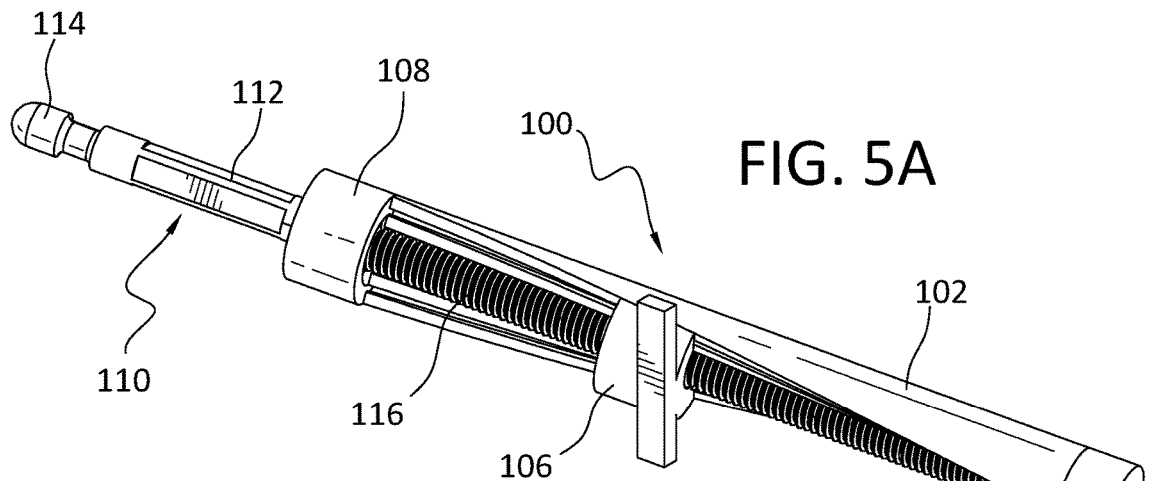
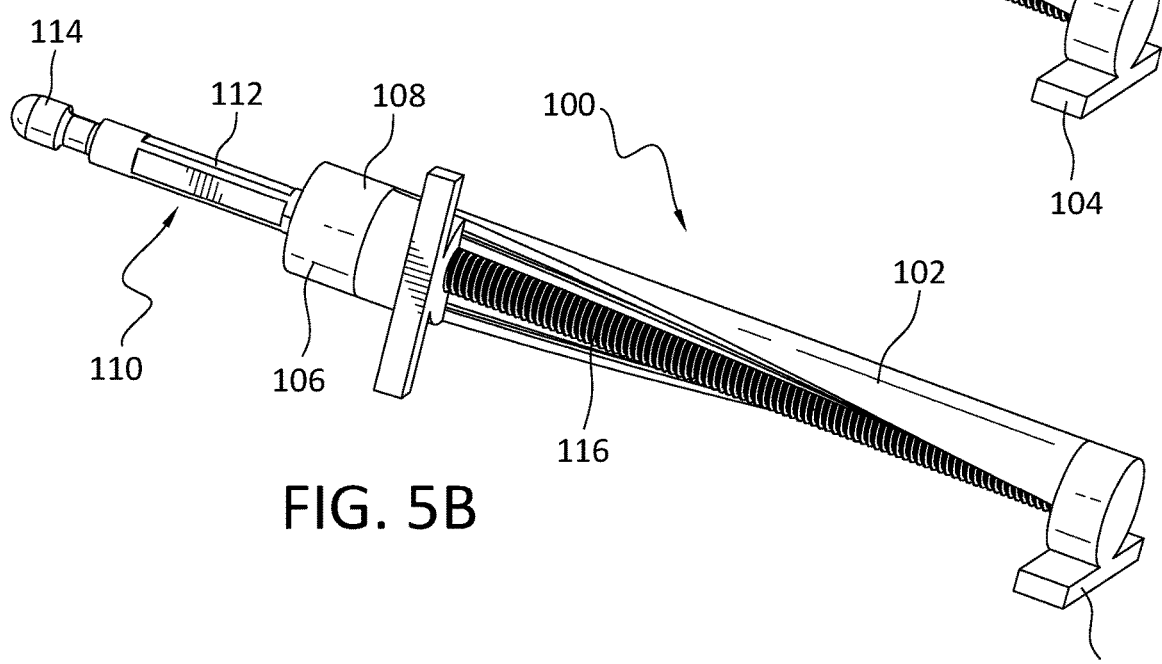
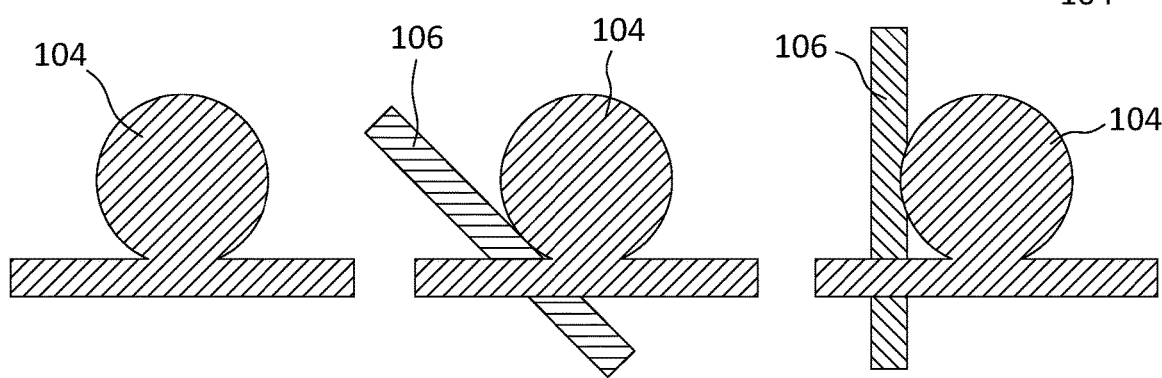

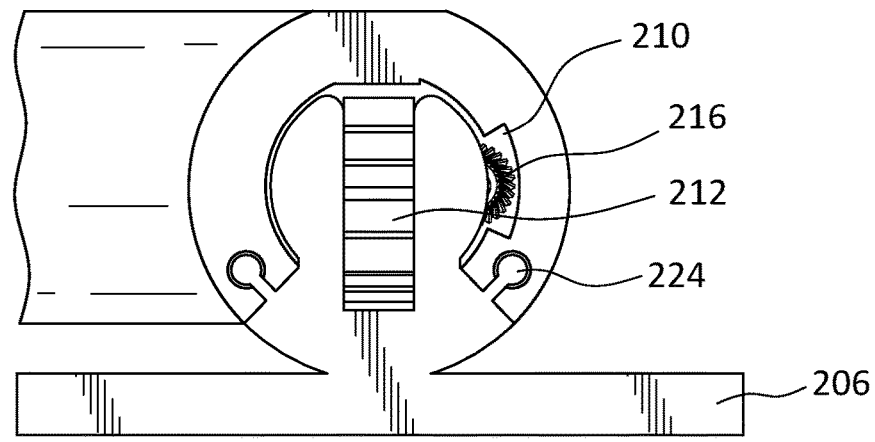
FIG. 11A
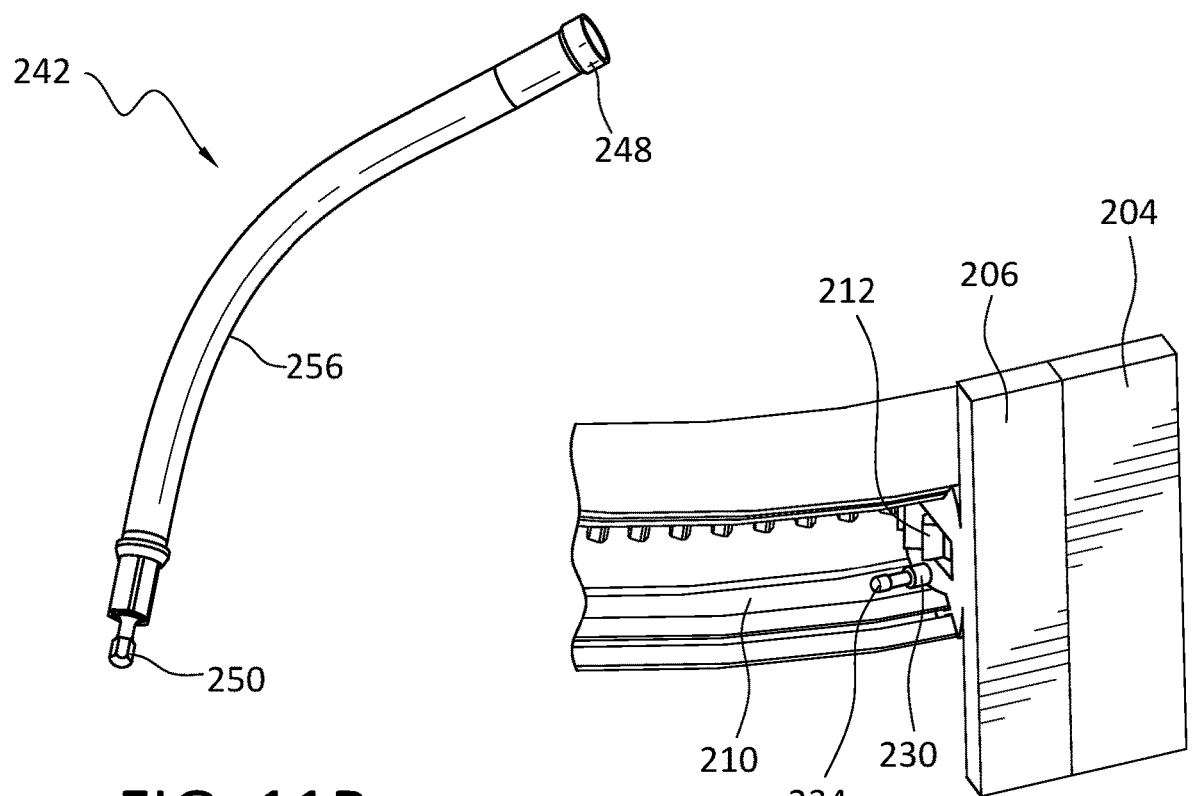
FIG. 11B
FIG. 11C

THREE DIMENSIONAL DISTRACTORS

TECHNICAL FIELD

Various exemplary embodiments disclosed herein relate generally to three dimensional distractors that allow for three dimensional distraction of a bone.

BACKGROUND

Distraction osteogenesis is a process used in orthopedic surgery, podiatric surgery, and oral and maxillofacial surgery to repair skeletal deformities and in reconstructive surgery. The procedure involves cutting and slowly separating bone, allowing the bone healing process to fill in the gap.

For example, craniofacial surgery may be used to correct a number of conditions of the jaw and face related to structure, growth, sleep apnea, correcting malocclusion problems owing to skeletal disharmonies or other orthodontic problems that cannot be easily treated with braces. During craniofacial surgery an osteotomy is often performed in which the bones can be cut, realigned, and held in place with either screws or plates and screws.

Distraction devices (commonly referred to as distractors) may be used to gradually adjust the relative orientation and spacing of bone parts on opposing sides of an osteotomy. Distractors typically include transcutaneous pins or screws secured to the bone on either side of the osteotomy together with a mechanism that allows controlled incremental adjustment of the distance between parts of the distractor on opposing sides of the osteotomy and the bone segments the parts of the distractor are attached to. Typically, distractors are used to perform distraction osteogenesis (the formation of bone).

Some surgical procedures may include a series of adjustments to the bone segments that have been separated by the osteotomy. These adjustments may be spaced out over a relatively significant amount of time, for example a number of weeks or months. In some cases the patient of the surgical procedure may be instructed to perform a series of adjustments to the distractor to adjust the distance between the bone segments. For example the patient may be instructed to adjust the distractor to increase the distance between the bone segments by 1 mm (millimeter) once every day.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

An helical distractor, including: a distractor body having an open tubular shape including: a fixed footplate attached to a first end of the distractor body; first and second body edges; first and second key grooves in the first and second body edges, respectively; and an end cap at a second end of the distractor body; a movable foot including: body threads; a first key configured to engage the first key groove; a second key configured to engage the second key groove; and a movable footplate; an advancement screw with a threaded portion inside the distraction body, wherein the threaded portion is configured to engage the body threads of the movable foot, wherein the movable foot moves along the distractor body when the advancement screw is rotated, and wherein the distractor body is configured to cause the movable foot to rotate as it moves along the distractor body.

Various embodiments are described, wherein the distractor is manufactured to have a shape configured to provide a specified treatment plan.

Various embodiments are described, wherein the distractor is manufactured so that the movable foot moves with specified translation along the advancement screw and rotation about the advancement screw relative to the fixed foot.

Various embodiments are described, wherein the fixed foot plate is manufactured with a shape to conform to a shape of a specific bone to be distracted.

Various embodiments are described, wherein the fixed foot plate configured to be attached to the fixed foot.

Various embodiments are described, wherein the movable foot plate is manufactured with a shape to conform to a shape of a specific bone to be distracted.

Various embodiments are described, wherein the endcap is configured to limit rotation of the advancement screw in one direction.

Various embodiments are described, wherein distractor body and the movable foot are manufactured using three dimensional printing.

Various embodiments are described, wherein the first and second key grooves have a helical shape.

Further various embodiments relate to an three-dimensional (3D) distractor, including: a distractor body having an open tubular shape including: a fixed footplate attached to a first end of the distractor body; first and second body edges; first and second key grooves in the first and second body edges, respectively; and internal teeth on an interior surface of the distractor body; a movable foot including: an advancement gear configured to engage the internal teeth and to move the movable foot along the distractor body when the advance gear rotates about a first axis of rotation; a drive mechanism configured to rotate the advancement gear about the first axis of rotation, wherein the drive mechanism transfers a drive rotation along a second axis of rotation to the first axis of rotation; a first key configured to engage the first key groove; a second key configured to engage the second key groove; and a movable footplate.

Various embodiments are described, wherein the distractor is manufactured to have a shape configured to provide a specified treatment plan.

Various embodiments are described, wherein the distractor is manufactured so that the movable foot moves with a specified translation and rotation relative to the fixed foot.

Various embodiments are described, wherein the specified translation is in three different dimensions and the specified rotation may be in three different directions.

Various embodiments are described, wherein the fixed foot plate is manufactured with a shape to conform to a shape of a specific bone to be distracted.

Various embodiments are described, wherein the fixed foot plate configured to be attached to the fixed foot.

Various embodiments are described, wherein the movable foot plate is manufactured with a shape to conform to a shape of a specific bone to be distracted.

Various embodiments are described, wherein distractor body and the movable foot are manufactured using three dimensional printing Various embodiments are described, further comprising a flexible extension arm configured to engage the drive mechanism and to provide the drive rotation.

Various embodiments are described, wherein the distractor body includes a body slot on the interior of the distractor body configured to accommodate the drive mechanism.

Various embodiments are described, wherein the drive mechanism includes: a first gear rotationally coupled to the advancement gear and configured to rotate about the first axis; and a second gear coupled to the first gear configure do to rotate about the second axis.

Various embodiments are described, wherein movable foot includes a first extension arm and a second extension arm, wherein the advancement gear is in between and supported by the first extension arm and the second extension arm.

Various embodiments are described, wherein the drive mechanism is connected to the first extension arm.

BRIEF DESCRIPTION OF THE DRAWINGS

In order to better understand various exemplary embodiments, reference is made to the accompanying drawings, wherein:

FIGS. 5A and 5B are perspective views of the helical distractor with the movable foot in different positions along the distractor body;

FIGS. 6A-6C illustrate that as the movable foot progresses along the distractor body the movable foot rotates relative to the fixed foot;

FIG. 11A illustrates an end view of the 3D distractor at one side of the movable foot assembly;

FIG. 11B illustrates an embodiment of an extension arm;

FIG. 11C illustrates a close up bottom perspective view of the 3D distractor.

To facilitate understanding, identical reference numerals have been used to designate elements having substantially the same or similar structure and/or substantially the same or similar function.

DETAILED DESCRIPTION

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

When a surgeon uses distraction osteogenesis with a patient, external or internal distraction may be used. With external distraction, footplates are attached to the two bone portions and the distraction device is external to the skin of the patient. With internal distraction, the footplates and the distraction device are all placed under the skin with a small port to allow for adjustment of the distraction device. External distraction easily allows for three dimensional translational and rotational movement between the distracted bones. One disadvantage of external distraction is that the external apparatus is unsightly and may make the patient feel uncomfortable and self-conscience. Currently internal distraction done only in a single translational direction. Accordingly, there is a need for a distractor that may be used internally that allows for additional degrees of freedom of movement between the bones to provide surgeons additional treatment possibilities while still using an internal distractor. Embodiments of distractors will be described below that allow for translation and rotations in different directions. The distractors described herein may be used in any application of distraction osteogenesis, including for example, in the intramedullary canal of long bones.

Figure 1A:
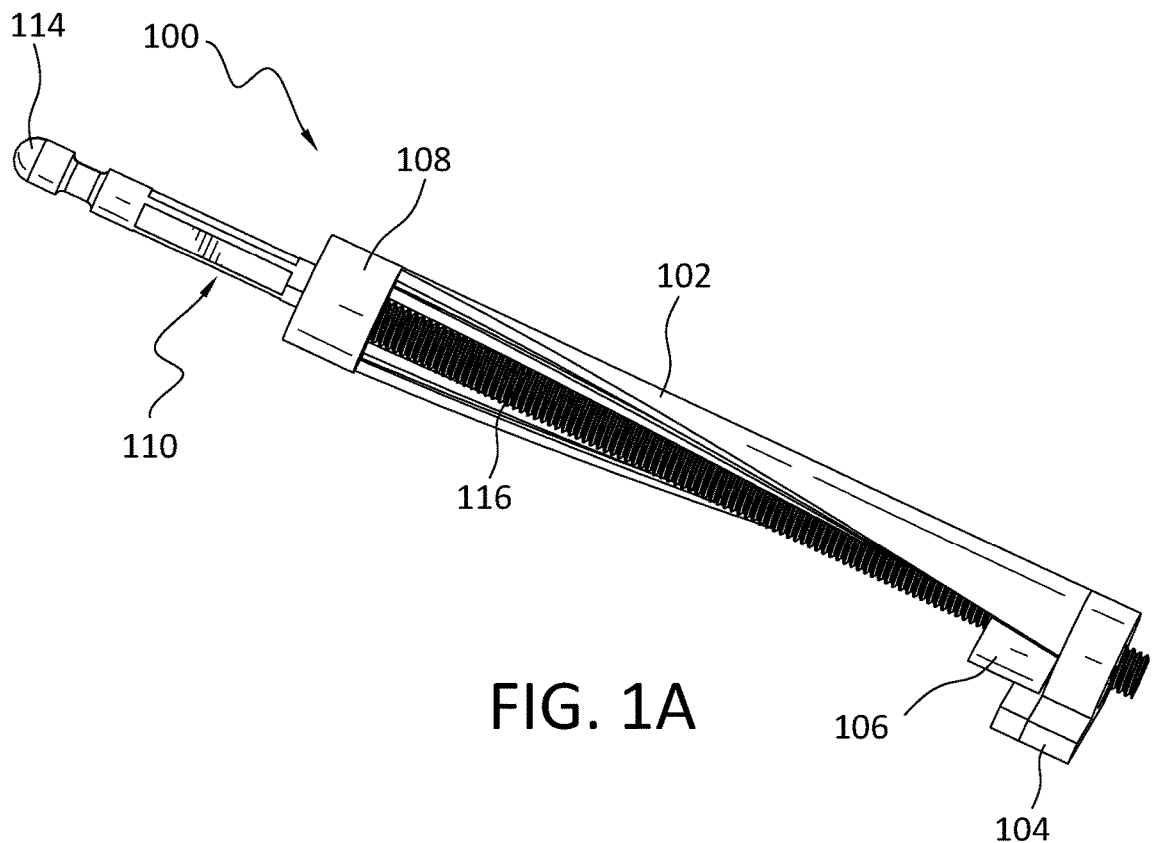
FIG. 1A illustrates a side perspective view of a helical distractor.
Figure 1B:
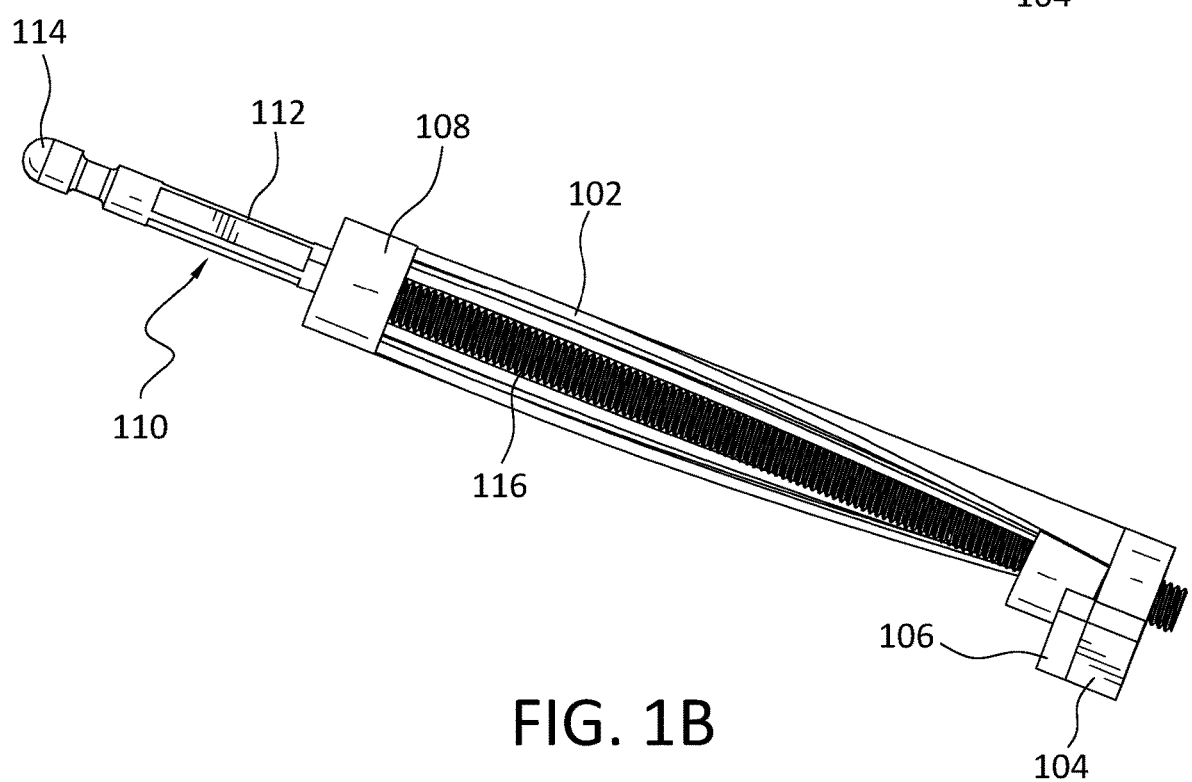
FIG. 1B illustrates a bottom perspective view of the helical distractor.
Figure 1C:
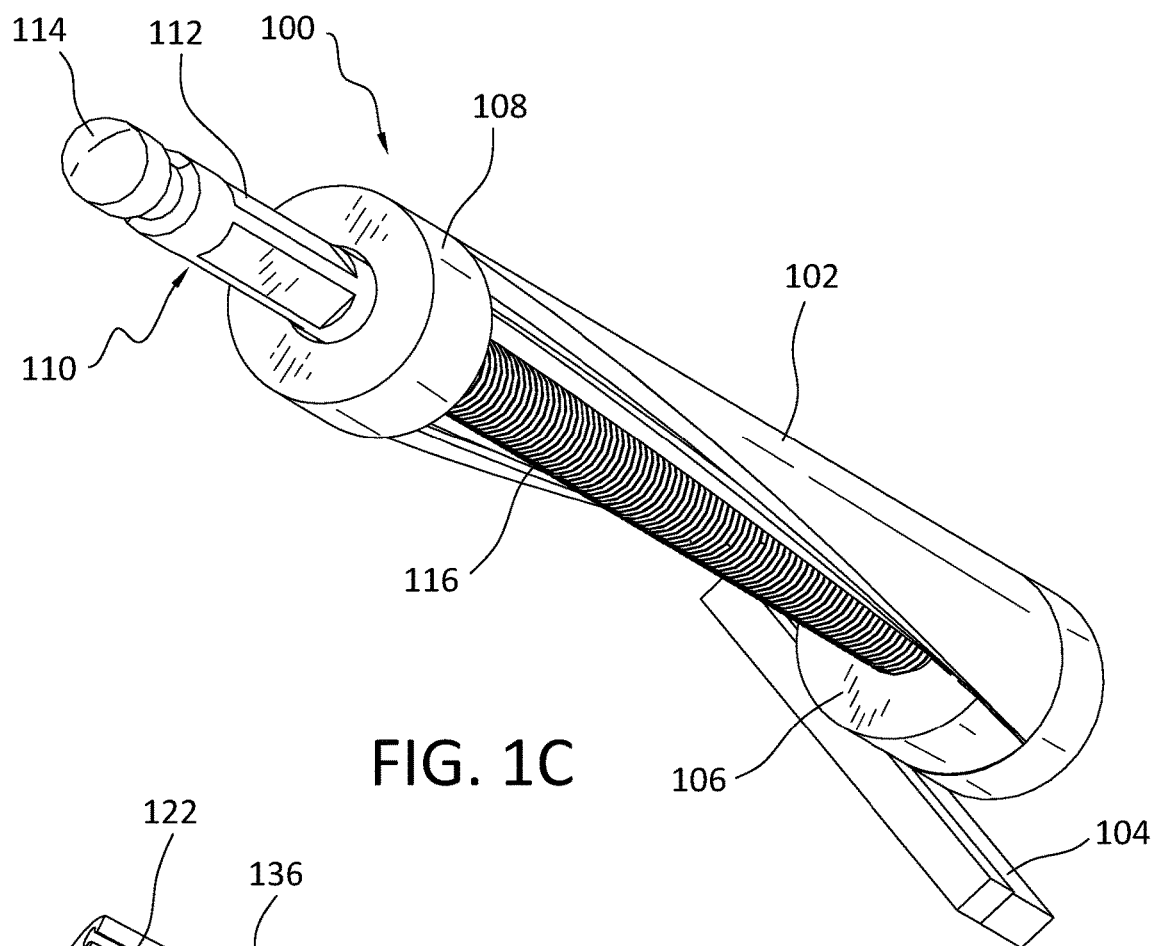
FIG. 1C illustrates an end perspective view of the helical distractor.

In certain treatment situations, surgeons would like to be able to have a rotational or helical movement of the bones in addition to a translational movement. An embodiment of a helical distractor will now be described that provides both a translational and helical movement during distraction. FIG. 1A illustrates a side perspective view of a helical distractor 100, FIG. 1B illustrates a bottom perspective view of the helical distractor 100, and FIG. 1C illustrates an end perspective view of the helical distractor 100. The helical distractor 100 includes a distractor body 102, a movable foot 106, and end cap 108, and an advancement screw 110. The end cap 108 is attached to the distractor body 102 to capture and hold the advancement screw 110 in place. The movable foot 106 engages the advancement screw 110 and moves along the distractor body 102 as the advancement screw 110 is rotated.

Figure 2A:
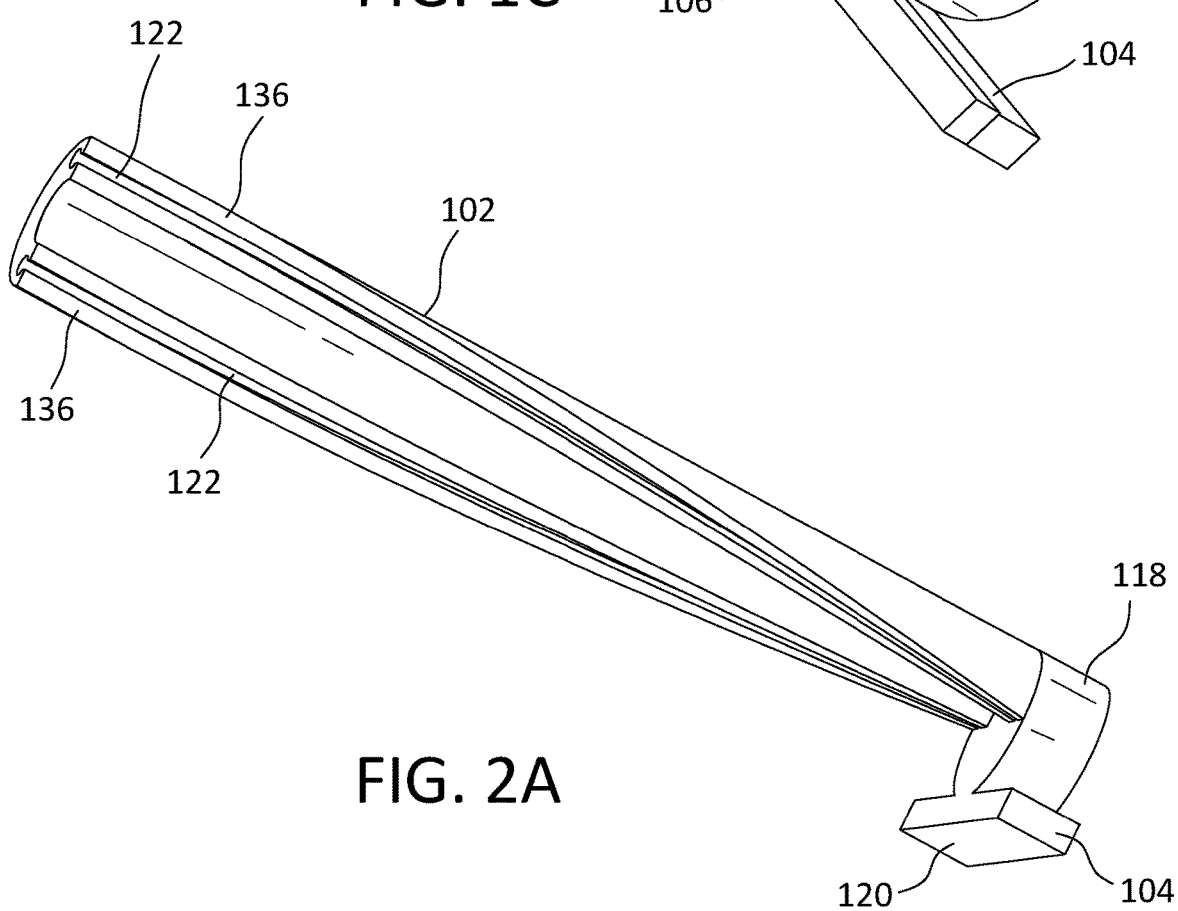
FIGS. 2A, 2B, and 2C illustrate a perspective bottom, top, and end views respectively of the distractor body.
Figure 2B:
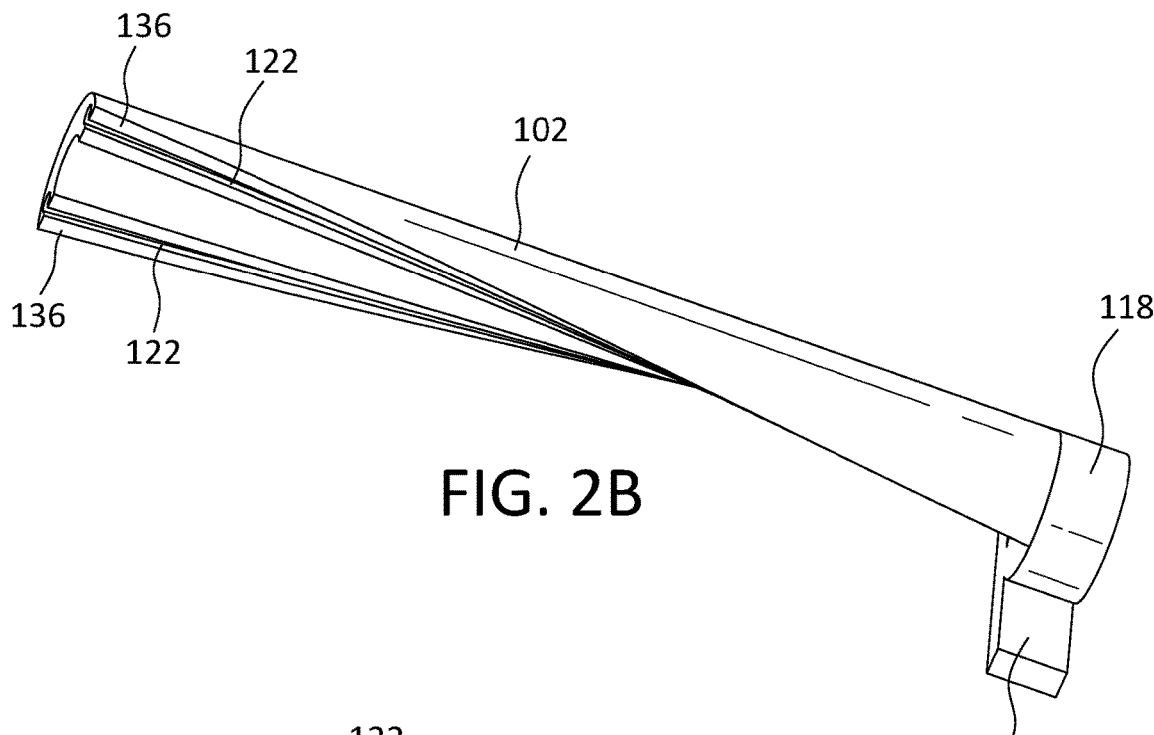
Figure 2C:
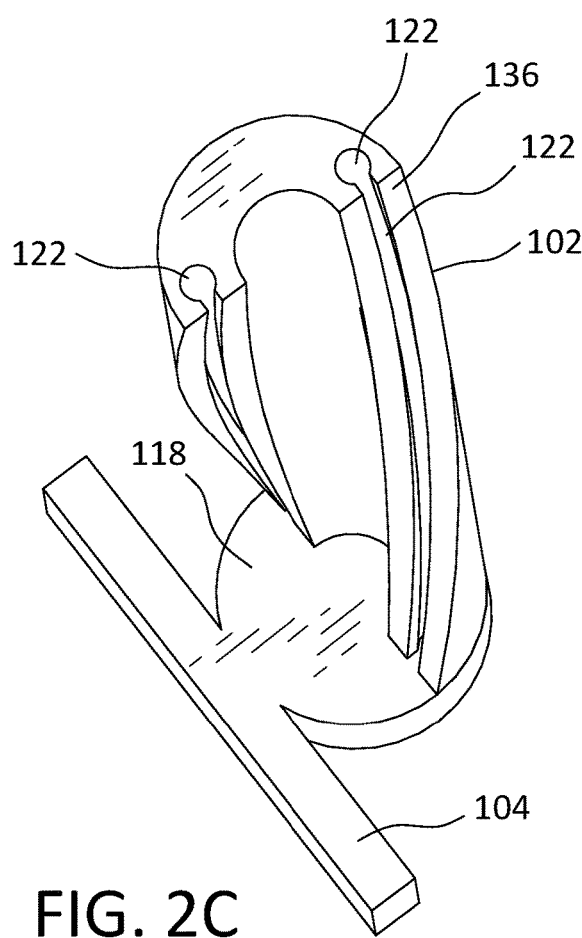
Figure 2D:
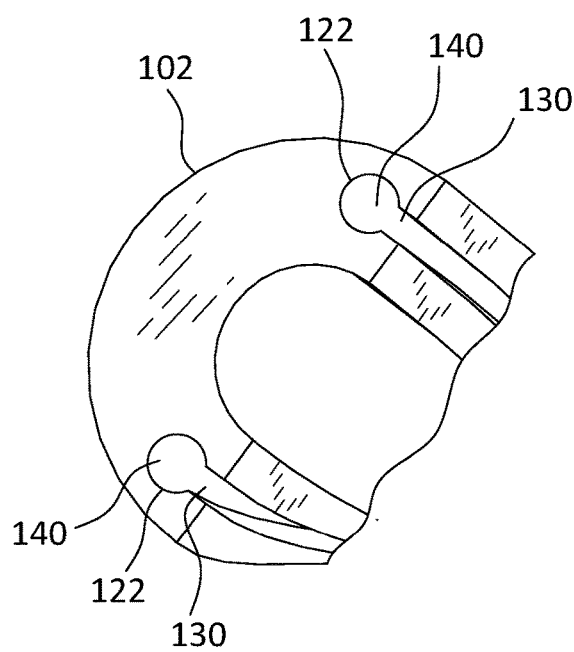
FIG. 2D illustrates a close up end view of the distractor body.

FIGS. 2A, 2B, and 2C illustrate a perspective bottom, top, and end views respectively of the distractor body 102, and FIG. 2D illustrates a close up end view of the distractor body 102. The distractor body 102 has a tubular shape with an open portion or semi-cylindrical shape that is helical or twisted from one end of the distractor body 102 to the other end. While the distractor body 102 is illustrated as having a semi-circular cross-section, the distractor body 102 could have other cross-sectional shapes. For example, it could be rectangular or hexagonal with one of the sides removed to provide the helical opening. The distractor body 102 has distractor body edges 136 that have a helical shape that is at the edges 136 twist form a helical shape. The distractor body also includes a fixed footplate 104 that includes a body end 118 and a fixed footplate 120. The semi-cylindrical portion of the distractor body 102 extends from the body end 118. It is this helical shape that provides the rotation of the movable foot 106 as it translates along the distractor body 102.

The fixed footplate 120 is shown as a solid rectangular member, but it will typically have screw holes or some other fixation feature that allows the fixed footplate 120 to be attached to the bone. Also the fixed footplate 120 may be manufactured with a shape that conforms with the bone to be connected to the fixed footplate 120. This shape may be specified by planning software that uses actual patient images to determine the desired shape for the fixed foot plate 120.

The distractor body edges 136 may include keyed groove 122. The keyed groove 122 is configured to receive a key 124 (see FIGS. 3A-C). In the embodiment of FIGS. 2A-D, the keyed groove 122 may include a slot 138 and a rounded opening 140. The slot 138 has a generally rectangular cross-sectional area, but may have other shapes as well. The rounded opening 140 has a generally circular cross-sectional area, but may have other shapes as well. The keyed groove 122 has a complementary shape to the key 124 (see FIGS. 3A-C) so that the keyed groove 122 captures and retains the key 124 so that the movable foot 106 is attached to and retained by the distractor body 102. The keyed groove 122 and key 124 may take any complementary shapes that allows for the movable foot 106 to be attached to and retained by the distractor body 102.

Figure 3A:
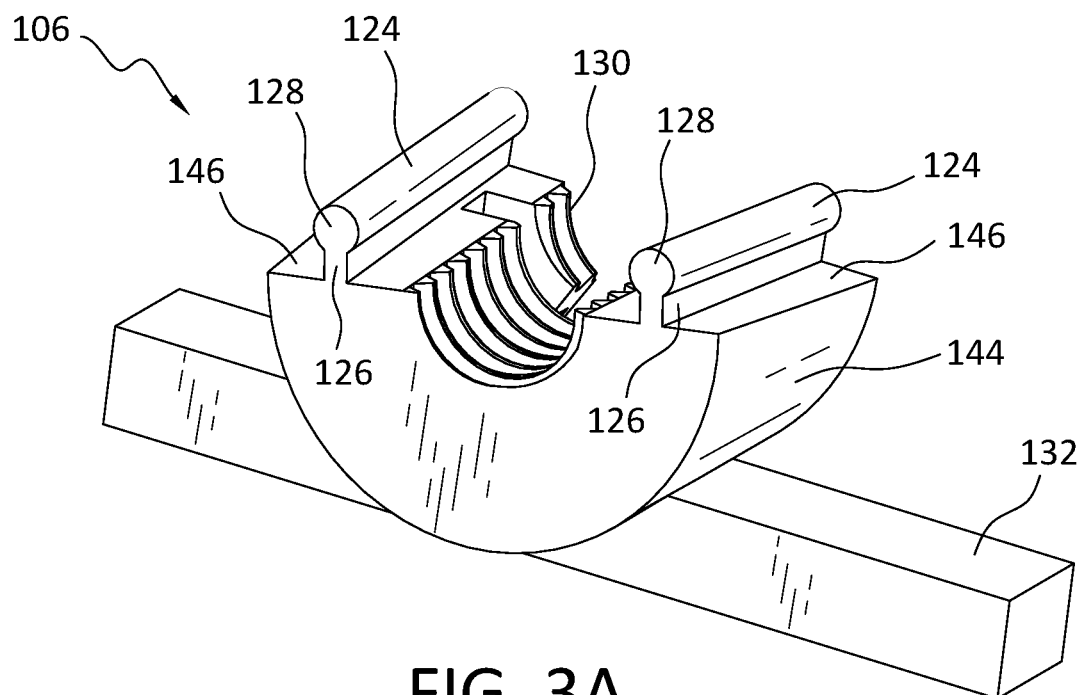
FIGS. 3A-C illustrate a front, top, and side perspective views, respectively, of the movable foot.
Figure 3B:
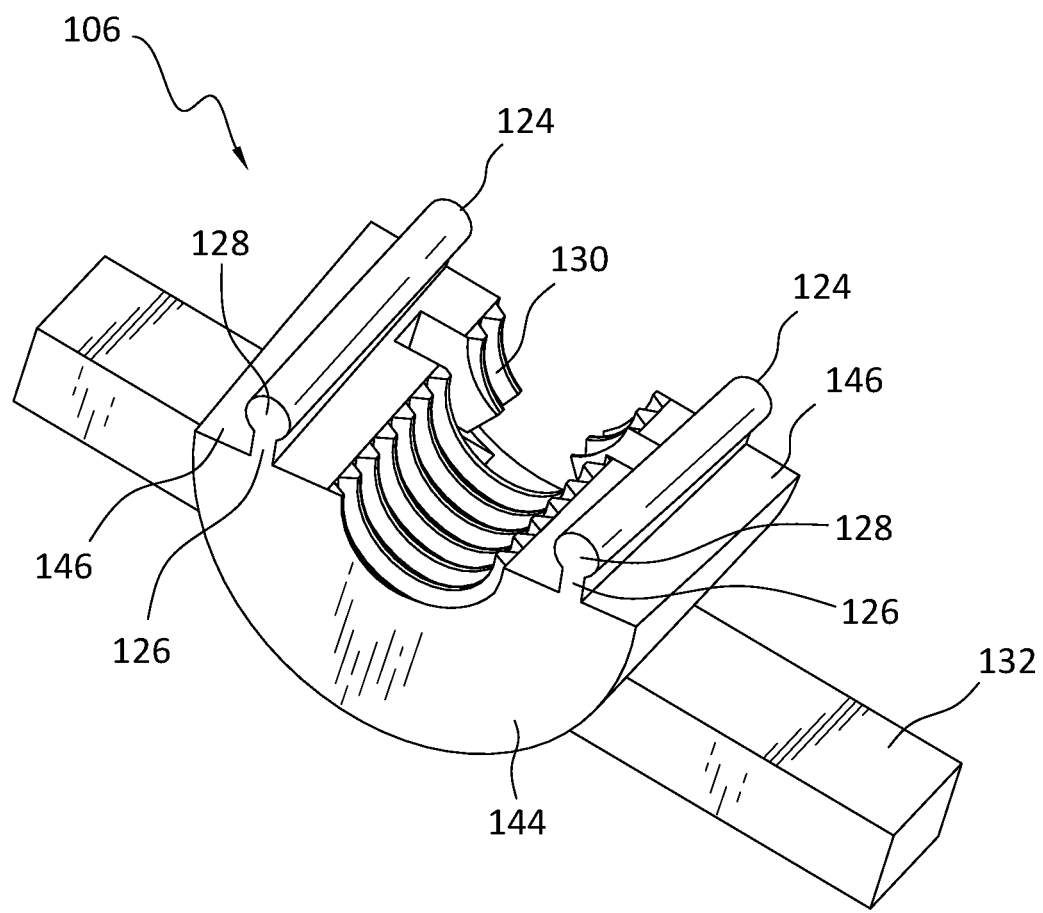
Figure 3C:
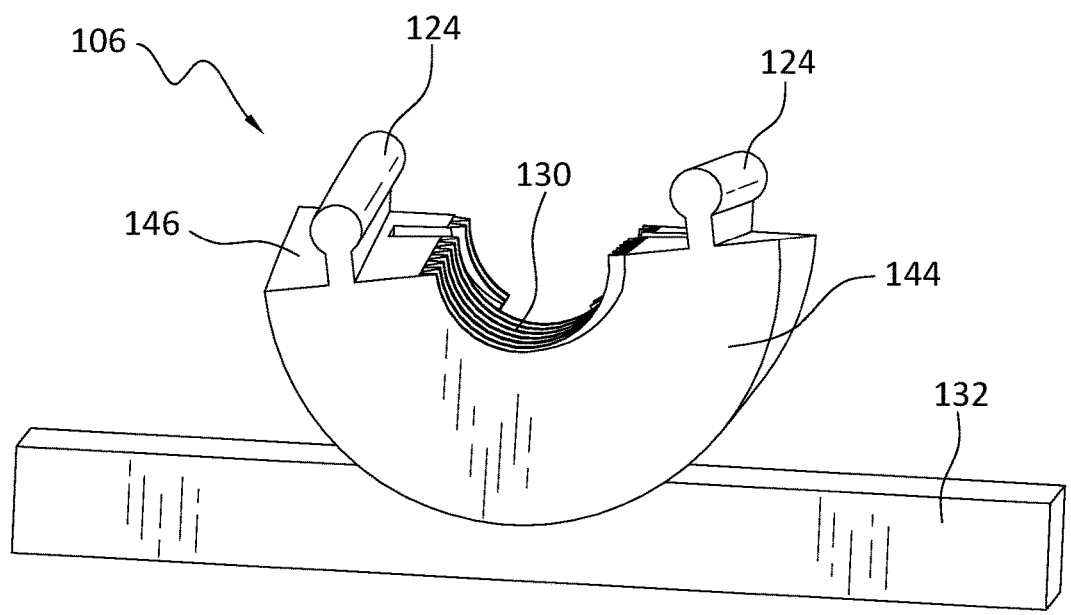

FIGS. 3A-C illustrate a front, top, and side perspective views, respectively, of the movable foot 106. The movable foot 106 also includes a movable footplate 132 that is shown as a solid rectangular member, but the movable footplate 132 will typically have screw holes or some other fixation feature that allows the movable footplate 132 to be attached to the bone. Also the movable footplate 132 may be manufactured with a shape that conforms with the bone to be connected to the movable footplate 132. This shape may be specified by planning software that uses actual patient images to determine the desired shape for the fixed foot plate 132.

The movable foot 106 also includes a movable foot body 144. The movable foot body 144 may have a semi-cylindrical shape with movable foot edges 146. The semi-cylindrical shape of the movable foot body 114 complements the shape of the distractor body 102. The shape of the movable foot body 114 may be any shape that allows the movable foot body 114 to complementary mate with the distractor body 102. The movable foot body 144 includes body threads 130 on an inside surface. The body threads 130 are configured to engage screw threads 116 so that the movable foot 106 moves along the distractor body 102 when the advancement screw 110 is rotated.

In an alternative embodiment, the movable foot body 144 may have a structure that extends the screw threads 130 to encircle the advancement screw 110 or that extends around greater than 50% of the circumference of the advancement screw 110 so that the screw threads 130 capture and fix the advancement screw 110 to the movable foot 106.

The movable foot 106 includes keys 124 extending from the movable foot edges 146. The key 124 is illustrated as having a key body 126 and key end 128. The key body 126 is shown as being generally rectangular, and the key end 128 is shown as being generally cylindrical. The overall shape of the key 124 is complementary to the key groove 122 as described above. The key 124 may take other shapes that are complementary to the key groove 122 also as described above.

Figure 4:
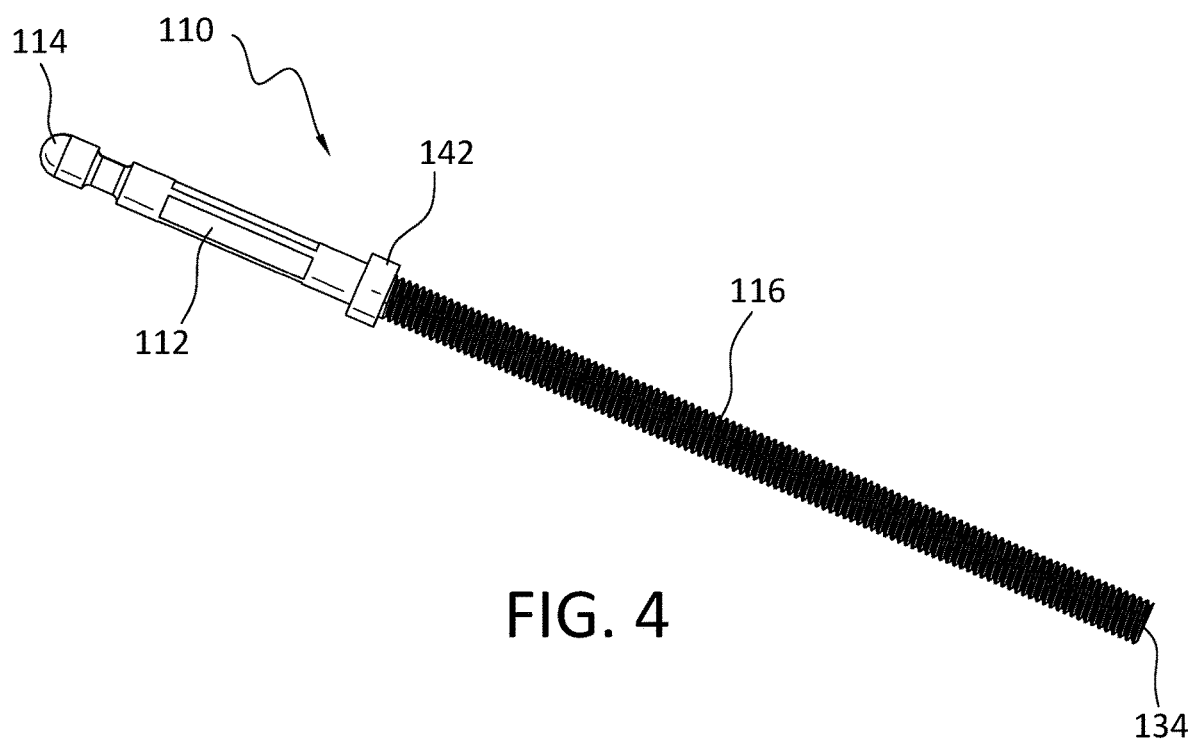
FIG. 4 illustrates the advancement screw.

FIG. 4 illustrates the advancement screw 110. The advancement screw 110 includes an engagement end 114, distal end 134, flat sided section 112, screw threads 116, and screw collar 42. The screw threads 116 engage the body threads 130 of the movable foot 106 so that as the advancement screw 110 is rotated, the movable foot 106 moves along the distractor body 102. The flat sides 112 may interact with structures in the end cap 108 that allow for rotation of the advancement screw 110 only in one direction. This may prevent the inadvertent closing of the gap between the bones during the treatment period. Also, the flat sides 112 may interact with the end cap 108 to allow for discrete increment of rotation and hence discrete increments of lateral movement of the movable foot 106.

The engagement end 114 allows for the engagement of a tool or a rod to rotate the advancement screw 110 during placement or during treatment. The engagement end 114 may have a hexagonal shape to engage a hexagonal tool. Further, the advancement screw 110 may include a screw collar 142 that engages the end cap 108 to keep the advancement screw 110 attached to the distractor body 102.

FIGS. 5A and 5B are perspective views of the helical distractor 100 with the movable foot 106 in different positions along the distractor body 102. In FIG. 5A, the movable foot 106 is about half-way between the ends of the helical distractor 100. In FIG. 5B, movable foot 106 has moved all the way to the end cap 108 of helical distractor 100. FIGS. 6A, 6B, and 6C show an end view of the helical distractor 100 corresponding the FIGS. 1A, 5A, and 5B respectively. In FIGS. 1A and 6A, the fixed foot 104 and the movable foot 106 are next to each other and completely align so that in FIG. 6A only the fixed foot 104 shows. In FIGS. 5A and 6B, the movable foot 106 has progressed about half way along the distractor body 102, and the movable footplate 132 is now at about a 45° angle from the fixed footplate 120. In FIGS. 5B and 6C, the movable foot 106 has progressed along the distractor body 102 to the end cap 108, and the movable footplate 132 is now at about a 90° angle from the fixed footplate 120. FIGS. 6A-6C illustrate that as the movable foot 106 progresses along the distractor body 102, the movable foot 106 rotates relative to the fixed foot 104. This will cause the two bones to attached to the helical distractor 100 to not only separate from one another but to rotate relative to one another. Accordingly, a surgeon now has the flexibility to not only have a linear translation between two bone that are distracted, but to also add a rotation to the distraction treatment.

The treatment of a patient using the helical distractor 100 will now be described. The surgeon may use known planning techniques and planning software to plan the treatment of the patient. The planning will include determining the specific cut to be made to the bone and then the desired final position of the dissected bones. The planning software can then determine the required movement of the bones during the treatment to achieve the final bone positions and the related bone growth that will fuse the dissected bones to one another. Because the helical distractor 100 allows for a rotation about an axis of translation provided by the helical distractor, the surgeon can add this rotation to provide more treatment options. During the planning process this translation and associated rotation may be specified. It is noted that an ending angle of 90° was described above, but the ending angle can be any angle. Then these parameters may be used to design a specific distractor body 102 that will achieve the desired translation and rotation. This design may then be used to manufacture the distractor body 102 using 3D printing or other manufacturing techniques. One other manufacturing technique may include starting with a cylindrical distractor body and cutting a portion away to form the helical distractor body 102. Then the keyed grooves 122 could then be cut into the distractor body 102. This results in highly specific treatment for each patient.

As part of the manufacturing the fixed foot plate 104 may be designed to match the specific attachment point on the bone. The planning software will be able to facilitate that by analyzing various images taken of the patient anatomy. Similarly, the movable foot 106 may be specifically manufactured for the specific patient and treatment plan. Specifically, the movable footplate 132 may be designed to match the specific attachment point on the bone.

Further, the keyed groove 122 and key 124 may be designed to facilitate the needed movement of the movable foot 106 along the distractor body 102. For example, the resulting keyed groove 122 and distractor body edge 136 may have a slight curvature as it follows a helical path. Accordingly, the key 124 and movable foot edge 146 may have a matching slight curvature that is compatible with the keyed groove 122 and the distractor body edge 136, respectively. Because the curvature of the keyed groove 122 and distractor body edge 136 is specific to each patient and treatment plan, the keyed groove 122, distractor body edge 136, key 124, and moveable foot edge 146 will be specific for each treatment plan and will be manufactured accordingly.

After the planning process determines the specific design of the helical distractor 100 to implement the desired treatment plan, the distractor body 102 and movable foot 106 may be manufactured. The cap end 108 and advancement screw 110 may be of standard designs and may be available in a variety of standard sizes and configurations. The helical distractor 100 may be assembled by placing the keys 124 of the movable foot 106 into the keyed groove 122 of the distractor body 102 at the end of the distractor body adjacent the end cap 108, and then sliding the movable foot 106 to the other end where the fixed foot 104 is located. Then the advancement screw 110 may be placed in the distractor body by screwing the screw distal end 134 into the movable foot 106. The screw distal end 134 may engage the body end 118, by for example being captured in depression in the body end 118 that keeps the screw distal end 134 in position relative to the distractor body 102. Then the end cap 108 may be slid over the engagement end 114 of the advancement screw 110 and slid into contact with the distractor body 102. The end cap 108 may be affixed to the distractor body using various methods, including a screw, a clip fitting, fasteners, etc. At this point, the screw collar 142 causes the advancement screw to be captured and fixed between the cap end 108 and the distractor body 102. Alternatively, the end cap 108 may be slid over the advancement screw 110, and then this combined assembly may be attached to the distractor body 102 and movable foot 106.

Now the assembled helical distractor 100 may be surgically placed in the patient. Then the advancement screw 110 may be rotated a specified amount periodically to achieve the desired bone growth and treatment plan.

In alternative embodiments, the fixed footplate 120 may be manufactured separately from the distractor body 102, and then the fixed footplate 120 is attached to the distractor body 102.

In another embodiment, the helical distractor 100 may be a center translating distractor. In this embodiment, the advancement screw 110 would have two independent screw threads that are threaded in opposite directions. Further, there would be two movable feet that start near one another in the center of the distractor body 102 and each engaging the different screw threads. Then when the advancement screw is rotated, each of the moveable feet move way from one another to cause the bones to move as desired.

In another embodiment, the end cap 108 may be integral to the distractor body 102. In this situation, the advancement screw 110 may include a groove that accepts a C-clip to perform the same function as the screw collar 142 in retaining the advancement screw 110 in the distractor body 102. This allows the advancement screw 110 to be inserted into the distractor body 102, and then the C-clip is placed in the groove on the advancement screw 110 inside the end cap 108 to prevent the advancement screw 110 from sliding out of the distractor body 102.

Figure 7A:
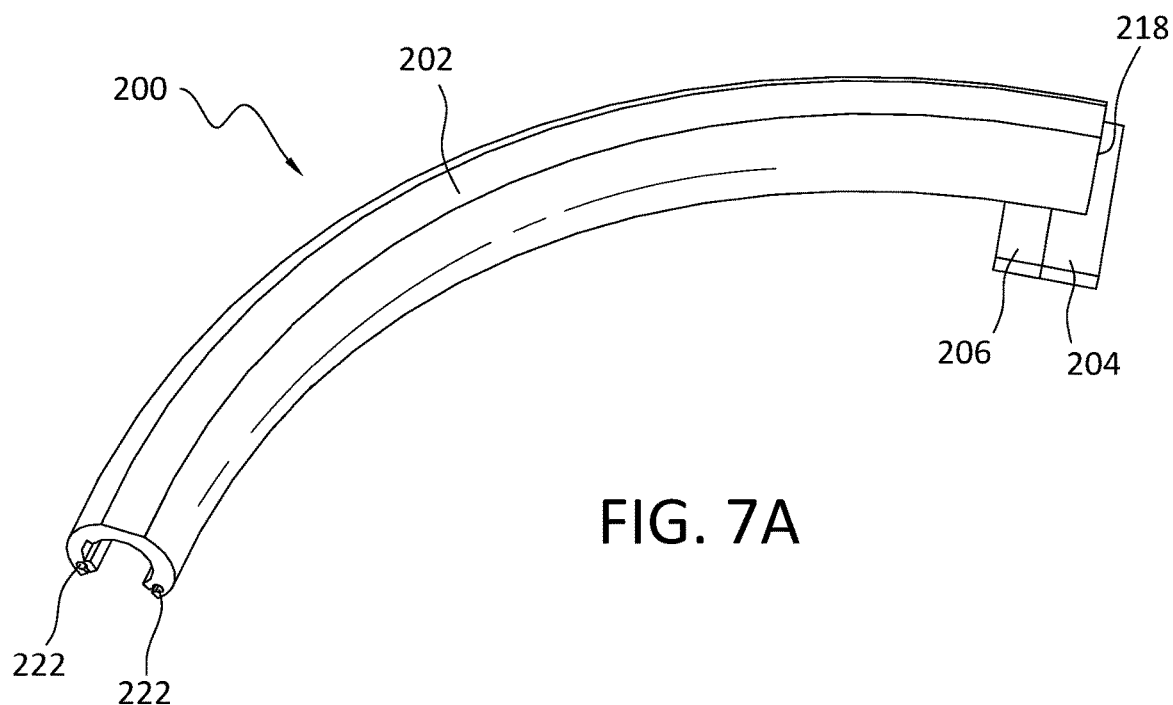
FIG. 7A illustrates a top perspective view of a 3D distractor.
Figure 7B:
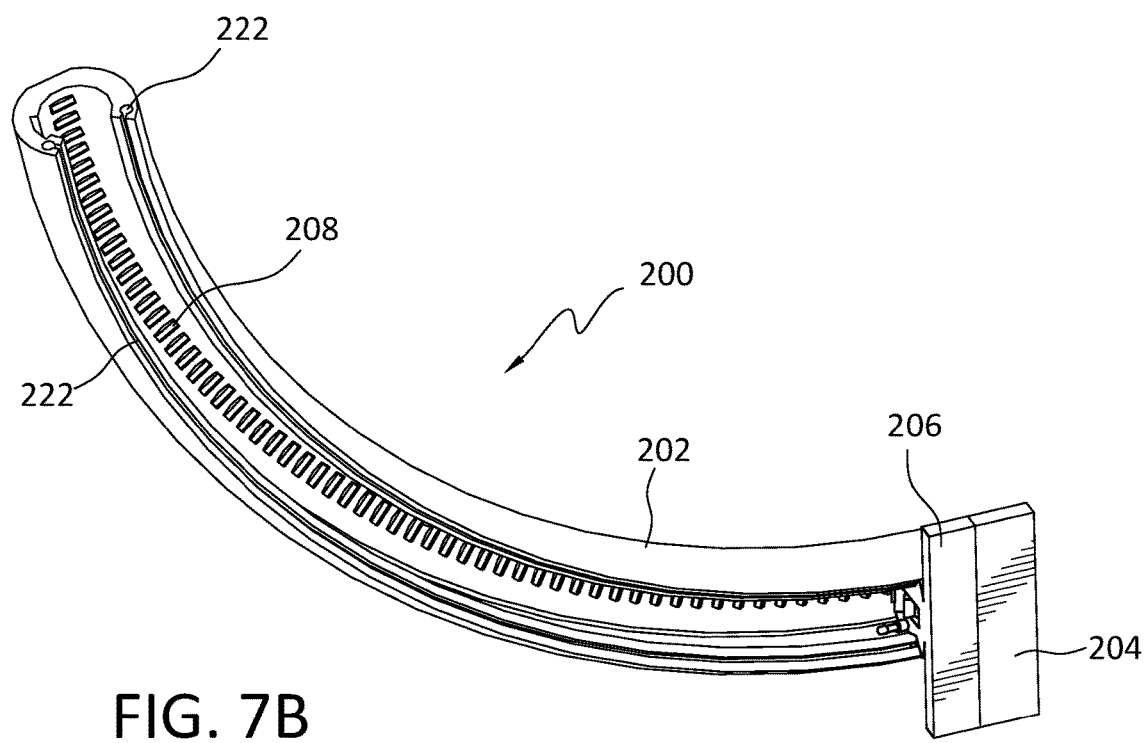
FIG. 7B illustrates a bottom perspective view of the 3D distractor.

In certain treatment situations, surgeons would like to be able to have a translational movement along three axes and rotational movement about those three axes, i.e., six degrees of freedom. An embodiment of a three dimensional (3D) distractor will now be described that may provide both a translational and rotational movement during distraction. FIG. 7A illustrates a top perspective view of a 3D distractor 200, and FIG. 7B illustrates a bottom perspective view of the 3D distractor 200. The 3D distractor 200 includes a distractor body 202 and a movable foot assembly 206. The movable foot assembly 206 includes an advancement gear 212 (see FIGS. 9A-9C) that engages internal teeth 208 in the distractor body 202 that moves the movable foot assembly 206 along the distractor body 202 as the advancement gear 212 is rotated.

Figure 8A:
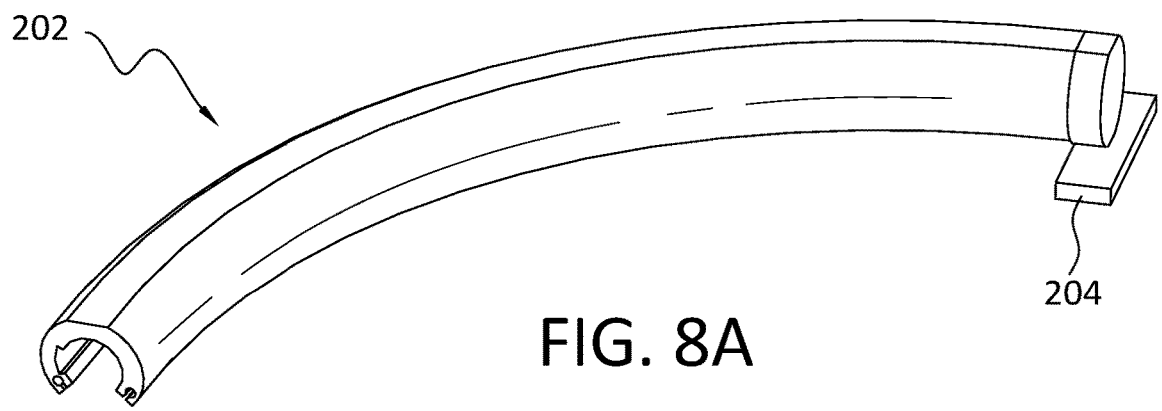
FIGS. 8A and 8B illustrate a top and bottom perspective view of the distractor body respectively.
Figure 8B:
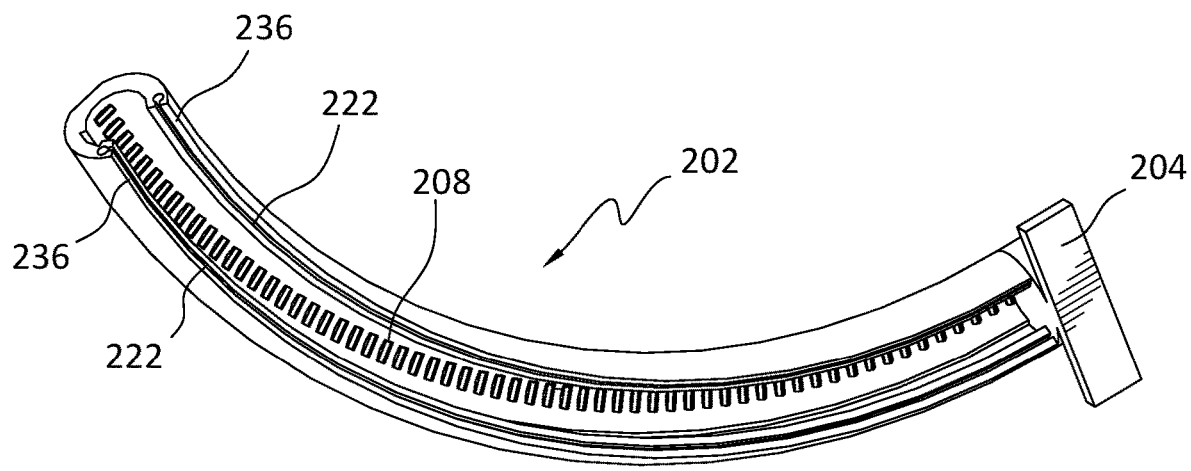
Figure 8C:
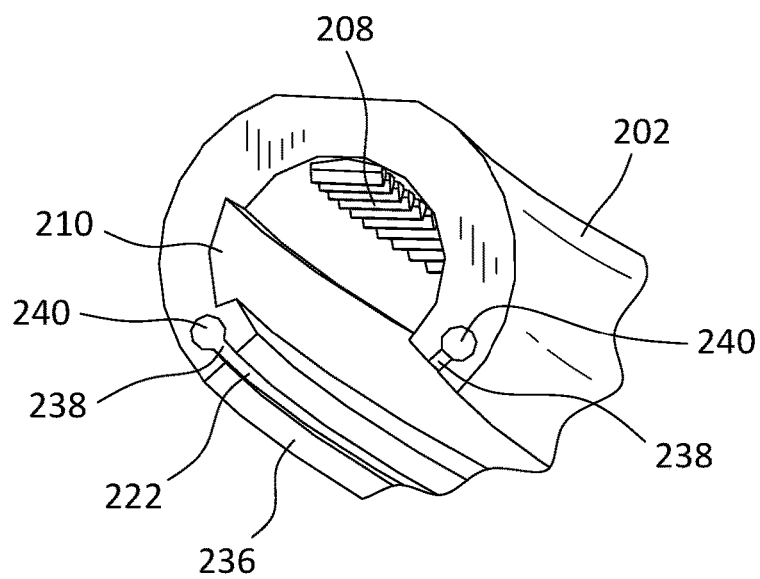
FIG. 8C illustrates a close up view of the distractor body.

FIGS. 8A and 8B illustrate a top and bottom perspective view of the distractor body 202, respectively, and FIG. 8C illustrates a close up view of the distractor body 202. The distractor body 202 has a tubular shape with an open portion or semi-cylindrical shape that may curve or twist from one end of the distractor body 202 to the other end. While the distractor body 202 is illustrated as having a semi-circular cross-section, the distractor body 202 could have other cross-sectional shapes. For example, it could be rectangular or hexagonal with one of the sides removed to provide the opening. The distractor body 202 has distractor body edges 236 that may have a curved and/or twisted shape. The distractor body 202 also includes a fixed footplate 204 that includes a body end 218 and a fixed footplate 220. The semi-cylindrical portion of the distractor body 202 extends from the body end 218. It is this curved and twisting shape that provides the 3D motion of the movable foot 206 as it translates along the distractor body 202.

The inside surface of the distractor body 202 includes internal teeth 208. The internal teeth 208 extend along the length of the distractor body 202 to provide the desired range of motion for the movable foot assembly 206. The advancement gear 212 engages the internal teeth 208 to cause the movable foot assembly 206 to move along the distractor body 202 as the advancement gear 212 rotates.

The fixed footplate 220 is shown as a solid rectangular member, but it will typically have screw holes or some other fixation feature that allows the fixed footplate 220 to be attached to the bone. Also the fixed footplate 220 may be manufactured with a shape that conforms with the bone to be connected to the fixed footplate 220. This shape may be specified by planning software that uses actual patient images to determine the desired shape for the fixed foot plate 220.

The distractor body edges 236 may include keyed groove 222. The keyed groove 222 is configured to receive a key 224 (see FIGS. 9A-9C and 10A-10C). In the embodiment of FIGS. 8A-8C, the keyed groove 222 may include a slot 238 and a rounded opening 240. The slot 238 has a generally rectangular cross-sectional area, but may have other shapes as well. The rounded opening 240 has a generally circular cross-sectional area, but may have other shapes as well. The keyed groove 222 has a complementary shape to the key 224 (see FIGS. 9A-8C and 10A-10C) so that the keyed groove 222 captures and retains the key 224 so that the movable foot assembly 206 is attached to and retained by the distractor body 202. The keyed groove 222 and key 224 may take any complementary shapes that allows for the movable foot assembly 206 to be attached to and retained by the distractor body 202.

Figure 9A:
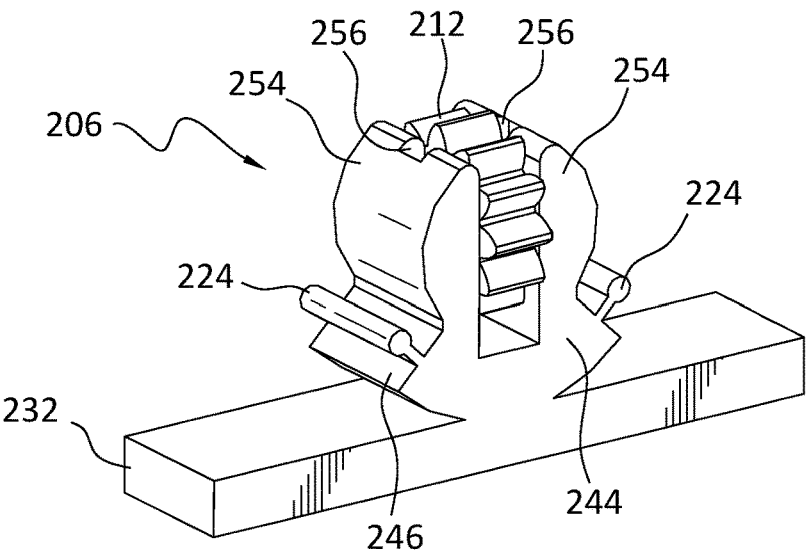
FIGS. 9A and 9B illustrate perspective views of the movable foot assembly respectively.
Figure 9B:
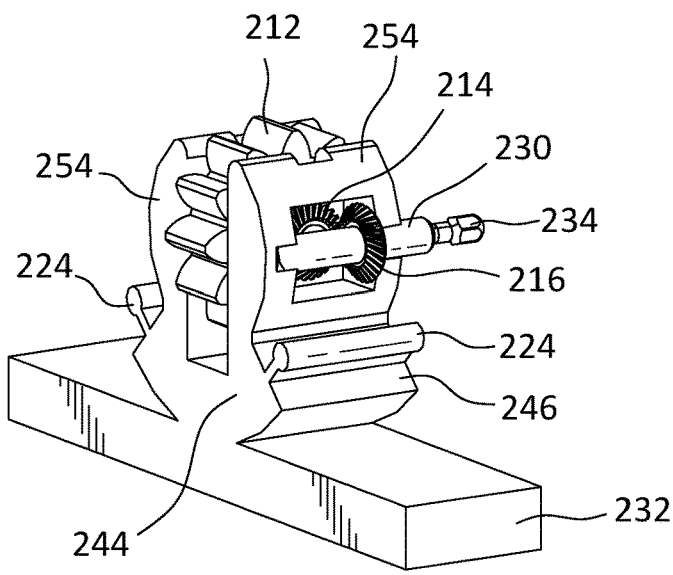
Figure 9C:
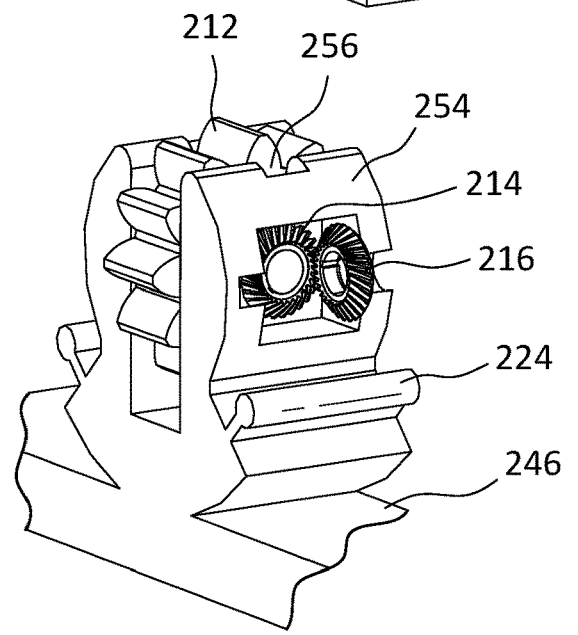
FIG. 9C illustrates a close up view of the movable foot assembly.
Figure 10A:
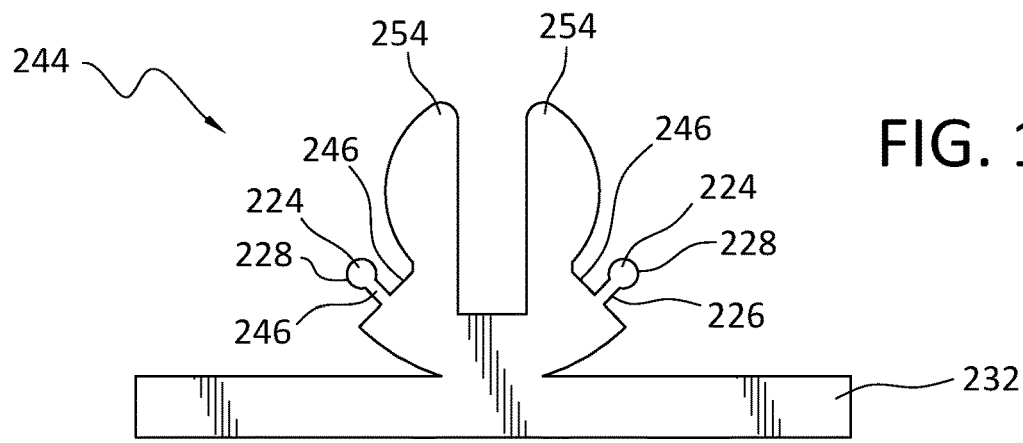
FIGS. 10A-C illustrate an end view, perspective view, and top perspective view, respectively, of a movable foot body.
Figure 10B:
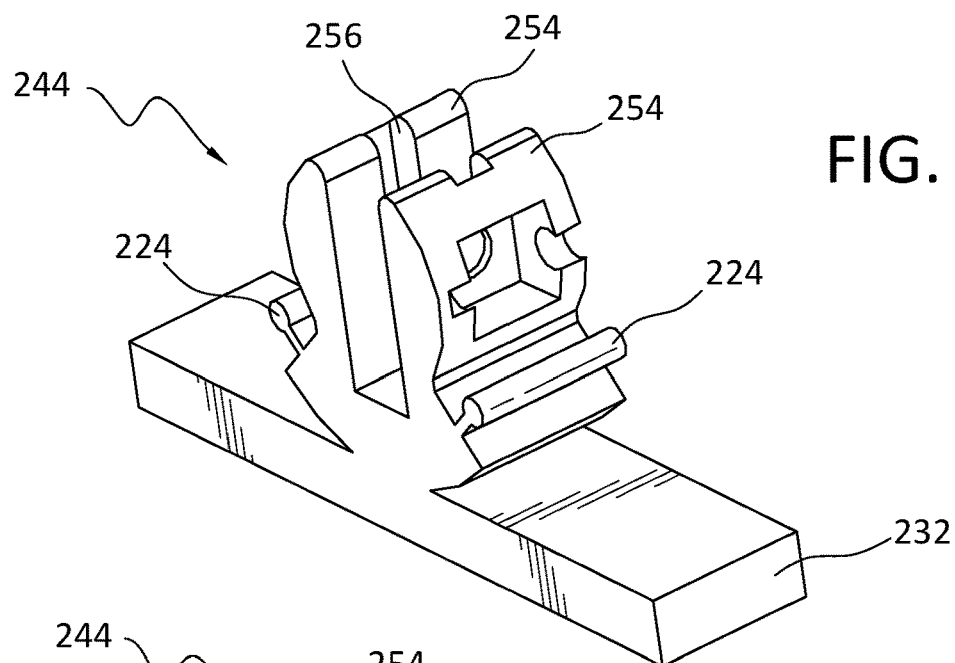
Figure 10C:
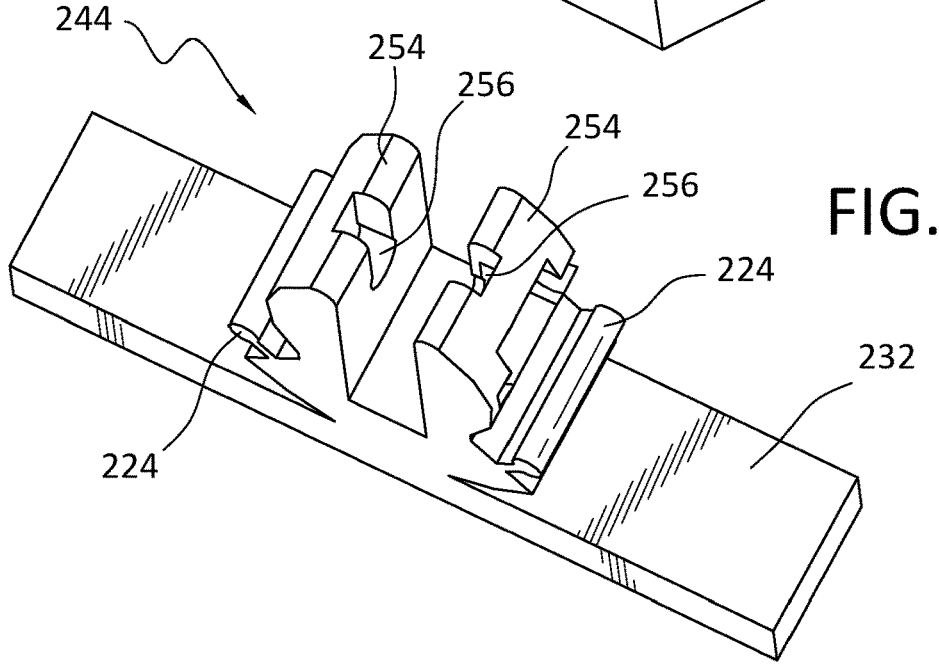

FIGS. 9A and 9B illustrate perspective views of the movable foot assembly 206, respectively, FIG. 9C illustrates a close up view of the movable foot assembly 206, and FIGS. 10A-C illustrate an end view, perspective view, and top perspective view, respectively, of a movable foot body 244. The movable foot assembly 206 includes a movable footplate 232, a movable foot body 244, and the advancement gear 212.

The movable footplate 232 is shown as a solid rectangular member, but the movable footplate 232 will typically have screw holes or some other fixation feature that allows the movable footplate 232 to be attached to the bone. Also the movable footplate 232 may be manufactured with a shape that conforms with the bone to be connected to the movable footplate 232. This shape may be specified by planning software that uses actual patient images to determine the desired shape for the movable foot plate 232.

The movable foot body 244 is connected to the movable footplate 232. The movable foot body 244 includes body arms 254 that secure the advancement gear 212 to the movable foot body 244. The advancement gear 212 is positioned to engage the internal teeth 208 of the distractor body 202. As the advancement gear 212 rotates, the movable foot assembly 206 moves along the distractor body 202. The advancement gear 212 includes an axle that fits in gear slots 256. A first bevel gear 214 may be attached to the axle. The movable foot assembly further includes a second bevel gear 216 attached to an activation member 230. The second bevel gear 216 engages the first bevel gear. The activation member 230 has an engagement end 234 that may be used to rotate the activation member 230. As the activation member 230 rotates, the second bevel 216 gear rotates which then rotates the first bevel gear 214. The rotation of the first bevel gear 214 causes the advancement gear 214 to rotate. Hence, when the activation member 230 rotates, the movable foot assembly 206 will move along the distractor body 202.

The engagement end 234 is shown as hexagonal and may be engaged by the distal end 248 (see FIG. 11B) of an extension arm 242. Any other shape may be used for the engagement end 234 to drive and rotate the activation member 230. Further, bevel gears 214, 216 are shown as a mechanism for converting the rotation of the activation member 230 into a rotation of the advancement gear 212, i.e., transferring rotation from one axis to another axis. But other mechanisms and types of gears may also be used to transfer the rotation from one axis to another axis. Further, the advancement gear 212 is shown as being approximately perpendicular to the movable footplate 232, but in alternative embodiments the advancement gear 212 may be approximately parallel to the movable footplate 232 or at some other angle relative to the movable footplate 232. Accordingly, the internal teeth 208 will be positioned to engage the advancement gear 212.

The movable foot assembly 206 includes keys 224 extending from the movable foot edges 246. The key 224 is illustrated as having a key body 226 and key end 228. The key body 226 is shown as being generally rectangular, and the key end 228 is shown as being generally cylindrical. The overall shape of the key 224 is complementary to the key groove 222 as described above. The key 224 may take other shapes that are complementary to the key groove 222 also as described above.

FIG. 11A illustrates an end view of the 3D distractor 200 at one side of the movable foot assembly 206. FIG. 11B illustrates an embodiment of an extension arm 242. FIG. 11C illustrates a close up bottom perspective view of the 3D distractor 200. The extension arm 242 includes extension arm flexible body 252, extension arm distal end 248, and extension arm proximal end 250. The distal end 248 is configured to engage the engagement end 234 of the activation member 230. The proximal end 250 may include an engagement member that may be engaged by a tool to rotate the extension arm 242. Alternatively, the proximal end may be designed to be gripped and rotated directly by hand. The flexible body 252 is flexible to allow extension arm 242 to conform to the curved shape of the distractor body 202. The distractor body 202 includes a body slot 210 on the inner surface of the distractor body 202. The extension arm 242 is inserted into the body slot 210 until it engages the activation member 230. Accordingly, when the extension arm 242 is rotated the advancement gear 212 rotates to move the movable foot assembly 206 along the distractor body 202. Further, second bevel gear 216 may extend into the body slot 210 if need be. In other embodiments, the bevel gears 214, 216 and the activation member 230 may be configured so that body slot 210 is not needed.

Figure 12A:
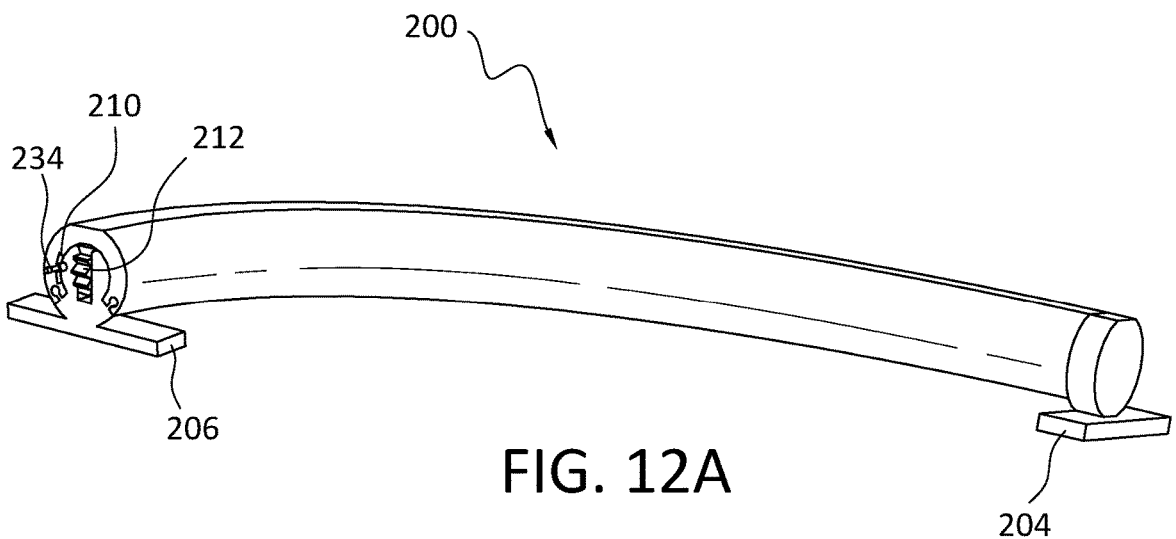
FIGS. 12A and 12B are top and bottom perspective views of the 3D distractor with the movable foot assembly in a second position along the distractor body.
Figure 12B:
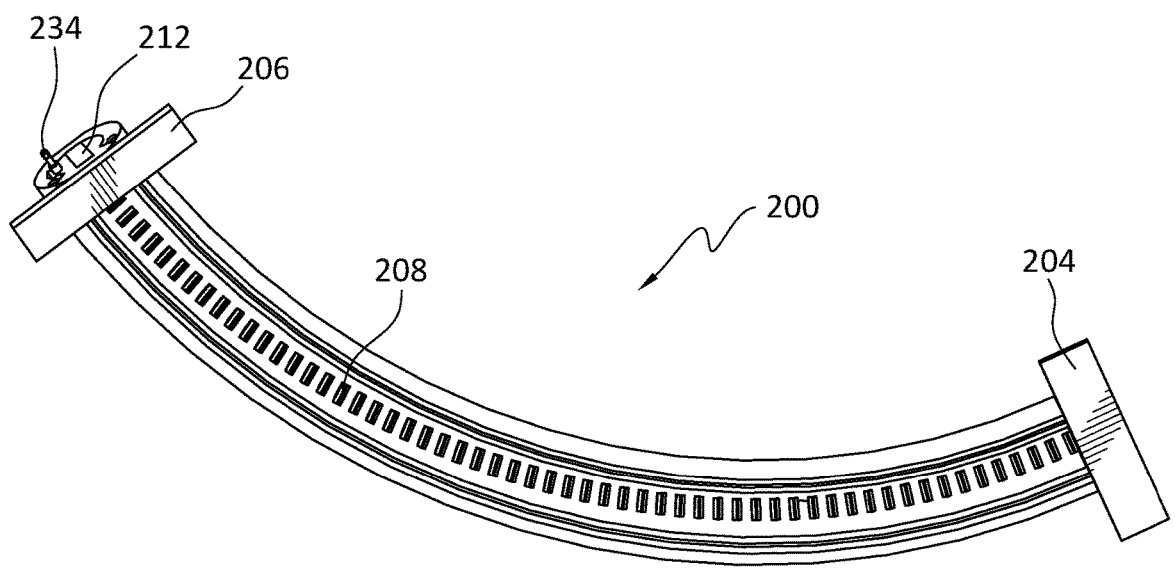

FIGS. 7A and 7B are top and bottom perspective views of the 3D distractor 200 with the movable foot assembly 206 in a first position along the distractor body 202. FIGS. 12A and 12B are top and bottom perspective views of the 3D distractor 200 with the movable foot assembly 206 in a second position along the distractor body 202. In FIGS. 7A and 7B, the movable foot assembly 206 is at a distal end of the 3D distractor 200 adjacent the fixed foot 204. In FIGS. 12A and 12B, the movable foot assembly 206 has moved all the way to the proximal end of the 3D distractor 200.

The treatment of a patient using the 3D distractor 200 will now be described. The surgeon may use known planning techniques and planning software to plan the treatment of the patient. The planning will include determining the specific cut to be made to the bone and then the desired final position of the dissected bones. The planning software can then determine the required movement of the bones during the treatment to achieve the final bone positions and the related bone growth that will fuse the dissected bones to one another. Because the 3D distractor 200 allows for translation along and rotation about three axes of translation, the surgeon should be able to implement a wide range of desired treatment options. During the planning process these translations and associated rotations may be specified. Then these parameters may be used to design a specific distractor body 202 that will achieve the desired translations and rotations. This design may then be used to manufacture the distractor body 202 using 3D printing or other manufacturing techniques. This results in highly specific treatment for each patient.

As part of the manufacturing the fixed foot plate 204 may be designed to match the specific attachment point on the bone. The planning software will be able to facilitate that by analyzing various images taken of the patient anatomy. Similarly, the movable foot assembly 206 may be specifically manufactured for the specific patient and treatment plan. Specifically, the movable footplate 232 may be designed to match the specific attachment point on the bone.

Further, the keyed groove 222 and key 224 may be designed to facilitate the needed movement of the movable foot assembly 206 along the distractor body 202. For example, the resulting keyed groove 222 and distractor body edge 236 may have a slight curvature as it follows a treatment path. Accordingly, the key 224 and movable foot edge 246 may have a matching slight curvature that is compatible with the keyed groove 222 and the distractor body edge 236, respectively. Because the curvature of the keyed groove 222 and distractor body edge 236 is specific to each patient and treatment plan, the keyed groove 222, distractor body edge 236, key 224, and moveable foot edge 246 will be specific for each treatment plan and will be manufactured accordingly.

After the planning process determines the specific design of the 3D distractor 200 to implement the desired treatment plan, the distractor body 202 and movable foot 106 may be manufactured. The advancement gear 212, first bevel gear 214, second bevel gear 216, and activation member may be of standard designs and may be available in a variety of standard sizes and configurations. The 3D distractor 200 may be assembled by placing the keys 224 of the movable foot assembly 206 into the keyed groove 222 of the proximal end of the distractor body 202, and then sliding the movable foot assembly 206 to the other end where the fixed foot 104 is located. This may be accomplished by using the extension arm 242.

Now the 3D distractor 200 may be surgically placed in the patient. Then the extension arm 242 may be rotated a specified amount periodically to achieve the desired bone growth and treatment plan.

In alternative embodiments, the fixed footplate 220 may be manufactured separately from the distractor body 202, and then the fixed footplate 120 is attached to the distractor body 202.

Various materials may be used to manufacture the helical distractor and the 3D distractor. This include various surgical grade metals as well as plastics that provide the required structural strength and rigidity. As discussed above 3D printing or other machining and manufacturing techniques may be used produce the various parts of the helical distractor and the 3D distractor.

Both the helical distractor and the 3D distractor provide a surgeon preparing a treatment plan for a patient with more options for movement and positioning of the bones. The helical distractor allows for a rotational motion in addition to the translational movement during the treatment plan. The 3D distractor provides complete six-degrees of freedom of movement during the treatment plan. This While each of the embodiments are described above in terms of their structural arrangements, it should be appreciated that the invention also covers the associated methods of using the embodiments described above.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications and combinations of the various embodiments can be affected while remaining within the spirit and scope of the invention. Accordingly, the foregoing disclosure, description, and figures are for illustrative purposes only and do not in any way limit the invention, which is defined only by the claims.

What is claimed is:

1. A helical distractor, comprising:
    a distractor body having an open tubular shape including:
        a fixed footplate attached to a first end of the distractor body;
        first and second body edges;
        first and second key grooves in the first and second body edges, respectively; and
        an end cap at a second end of the distractor body;
    a movable foot including:
        body threads;
        a first key configured to engage the first key groove;
        a second key configured to engage the second key groove; and
        a movable footplate;
    an advancement screw with a threaded portion inside the distraction body, wherein the threaded portion is configured to engage the body threads of the movable foot,
    wherein the movable foot moves along the distractor body when the advancement screw is rotated, and
    wherein the distractor body is configured to cause the movable foot to rotate as it moves along the distractor body.

2. The helical distractor of claim 1, wherein the distractor is manufactured to have a shape configured to provide a specified treatment plan.

3. The helical distractor of claim 1, wherein the distractor is manufactured so that the movable foot moves with a specified translation along the advancement screw and rotation about the advancement screw relative to the fixed footplate.

4. The helical distractor of claim 1, wherein the fixed footplate is manufactured with a shape to conform to a shape of a specific bone to be distracted.

5. The helical distractor of claim 4, wherein a fixed foot is configured to be attached to the fixed footplate.

6. The helical distractor of claim 1, wherein the movable footplate is manufactured with a shape to conform to a shape of a specific bone to be distracted.

7. The helical distractor of claim 1, wherein the end cap is configured to limit rotation of the advancement screw in one direction.

8. The helical distractor of claim 1, wherein the distractor body and the movable foot are manufactured using three dimensional printing.

9. The helical distractor of claim 1, wherein the first and second key grooves have a helical shape.

10. A three-dimensional (3D) distractor, comprising:
    a distractor body having an open tubular shape including:
        a fixed footplate attached to a first end of the distractor body;
        first and second body edges;
        first and second key grooves in the first and second body edges, respectively; and
        internal teeth on an interior surface of the distractor body;
    a movable foot including:
        an advancement gear configured to engage the internal teeth and to move the movable foot along the distractor body when the advancement gear rotates about a first axis of rotation;
        a drive mechanism configured to rotate the advancement gear about the first axis of rotation, wherein the drive mechanism transfers a drive rotation along a second axis of rotation to the first axis of rotation;

a first key configured to engage the first key groove;

a second key configured to engage the second key groove; and a movable footplate.

11. The 3D distractor of claim 10, wherein the distractor is manufactured to have a shape configured to provide a specified treatment plan.

12. The 3D distractor of claim 10, wherein the distractor is manufactured so that the movable foot moves with a specified translation and a specified rotation relative to the fixed footplate.

13. The 3D distractor of claim 10, wherein the fixed footplate is manufactured with a shape to conform to a shape of a specific bone to be distracted.

14. The 3D distractor of claim 13, wherein a fixed foot is configured to be attached to the fixed footplate.

15. The 3D distractor of claim 10, wherein the movable footplate is manufactured with a shape to conform to a shape of a specific bone to be distracted.

16. The 3D distractor of claim 10, wherein distractor body and the movable foot are manufactured using three dimensional printing.

17. The 3D distractor of claim 10, further comprising a flexible extension arm configured to engage the drive mechanism and to provide the drive rotation.

18. The 3D distractor of claim 10, wherein the distractor body includes a body slot on the interior surface of the distractor body configured to accommodate the drive mechanism.

19. The 3D distractor of claim 10, wherein the drive mechanism comprises:

a first gear rotationally coupled to the advancement gear and configured to rotate about the first axis; and a second gear coupled to the first gear configured to rotate about the second axis.

20. The 3D distractor of claim 10, wherein the movable foot includes a first extension arm and a second extension arm, wherein the advancement gear is in between and supported by the first extension arm and the second extension arm.

21. The 3D distractor of claim 20, wherein the drive mechanism is connected to the first extension arm.

* * * * *